United States Patent [19]

Taulbee, deceased et al.

[11] Patent Number: 4,993,586
[45] Date of Patent: Feb. 19, 1991

[54] ADHESIVE BANDAGE DISPENSING DEVICE AND ASSOCIATED METHOD

[75] Inventors: Orrin E. Taulbee, deceased, late of Blacksburg, Va., by Laura J. Harper, executor; Gregor M. Taulbee, executor, Columbus, Ohio; Frank R. Walters, Pittsburgh, Pa.

[73] Assignee: University of Pittsburgh, Pittsburgh, Pa.

[21] Appl. No.: 369,457

[22] Filed: Jun. 21, 1989

[51] Int. Cl.$^5$ .................. G07F 11/66; B65D 85/672
[52] U.S. Cl. ................................ 221/25; 221/73; 206/411; 206/441; 206/601; 156/527; 83/649
[58] Field of Search ................. 221/25, 26, 30, 31, 221/32, 69, 70, 71, 72, 73; 206/410, 411, 438, 440, 441, 601, 603; 156/525, 527, 584; 83/620, 649

[56] References Cited

U.S. PATENT DOCUMENTS

| | | |
|---|---|---|
| 2,005,676 | 6/1935 | Hanover . |
| 2,133,609 | 10/1938 | Eustis . |
| 2,822,046 | 2/1958 | Krveger ........................ 83/649 X |
| 3,520,403 | 7/1970 | Moshel . |
| 3,530,494 | 9/1970 | Baratta . |
| 3,542,628 | 11/1970 | Fink ............................ 156/527 |
| 3,835,992 | 7/1974 | Adams, IV . |
| 3,899,077 | 8/1975 | Spiegelberg . |
| 4,194,624 | 3/1980 | Spiegelberg . |
| 4,324,603 | 4/1982 | Crandall et al. . |
| 4,759,652 | 7/1988 | Ulrich ........................... 221/25 X |
| 4,807,753 | 2/1989 | Goldstein ..................... 206/440 X |
| 4,824,517 | 4/1989 | Leahy .......................... 221/73 X |

FOREIGN PATENT DOCUMENTS 67458 4/1982 Japan ........................ 83/649

Primary Examiner—Michael S. Huppert
Assistant Examiner—Kenneth DeRosa
Attorney, Agent, or Firm—Arnold B. Silverman

[57] ABSTRACT

An adhesive bandage dispensing device is provided which facilitates efficient and quick access to an adhesive bandage. The device has a base, a spool holder, a removal platform having a slicer and cutter and an adhesive bandage carrier spool mounted to the device by the spool holder. A continuous strip of adhesive bandages is mounted on the spool. The strip consists of separate adhesive bandages wrapped in a protective coating. The action of pulling the strip away from the spool over the platform causes a portion of the protective covering of strip to be sliced by the slicer. This will expose a bandage which then can be lifted off the remaining portion of the protective coating for use. After this, the cutter is used to separate the bandageless strip from the device for subsequent disposal.

18 Claims, 4 Drawing Sheets

ADHESIVE BANDAGE DISPENSING DEVICE AND ASSOCIATED METHOD

BACKGROUND OF THE INVENTION

1. Field Of The Invention

This invention relates to an adhesive bandage dispensing device and more particularly to a device having a spool containing a strip of adhesive bandages which can be accessed quickly and efficiently.

2. Description Of The Prior Art

Adhesive bandages are customarily packaged individually in a protective covering having a tear string to facilitate opening the single bandage package. Several of the individually packaged bandages are usually contained in a paperboard or metal box having a hinged lid. With this conventional packaging arrangement, the bandages are awkward to manipulate because of the need to use both hands in order to remove the adhesive bandage from the box and from the protective covering.

The prior art contains some teachings which are departures from the above arrangements such as U.S. Pat. No. 3,530,494 which discloses a dispensing device having a carrier spool of adhesive bandages along with a cutter to sever individual bandages; U.S. Pat. No. 2,133,609 which also discloses a device that dispenses adhesive bandages that are wrapped on a spool; and U.S. Pat. No. 3,835,992 which discloses a strip carrier for bandages wherein bandages are mounted in a channel like strip, the strip being separable from the spool by tearing the strip at transverse score lines.

Despite these prior art devices there remains a need for an adhesive bandage dispenser which effectively dispenses adhesive bandages by slicing the protective covering of the bandages and cutting the individual adhesive bandage away from the spool so that an adhesive bandage can be accessed quickly and efficiently with one hand.

SUMMARY OF THE INVENTION

The adhesive bandage dispensing device of the present invention has solved the above described need. The device preferably consists of a base, a spool holder, a removal platform having slicer and cutter means and an adhesive bandage carrier spool. Mounted on the spool is a continuous strip of adhesive bandages, the strip comprising a plurality of separate adhesive bandages protected by a top and bottom protective coating. The adhesive bandage strip is removed from the spool and onto the removal platform where the protective coating is sliced by the slicer then can be lifted off the remaining portion of the protective coating for use. After this, the cutter means can be used to separate the bandageless strip from the device for subsequent disposal.

It is an object of this invention to provide a device which dispenses adhesive bandages that are on a continuous strip which is wrapped around a spool.

It is a further object of this invention, in another embodiment, to provide a device which dispenses bandages from a continuous strip that is stacked in an adhesive bandage strip holder.

It is a further object of the invention to provide a device which slices the protective covering of the strip to expose an adhesive bandage and enables the desired number of bandages to be removed from the strip.

It is a further object of this invention to provide an adhesive bandage dispenser which can be quickly and efficiently operated by one hand.

It is a further object of this invention to provide an adhesive bandage dispensing device which can be used with different sizes and shapes of bandages.

It is a further object of this invention to provide easy mounting of the device on a wall, bench or piece of furniture such as a table, dresser, or stand.

It is a further object of this invention to provide a refillable or disposal adhesive bandage container.

It is a further object of this invention to provide a dispensing device which is economical to manufacture.

These and other objects will be more fully understood from the following description of the invention with reference to the drawings appended to this application.

DESCRIPTION OF THE PREFERRED EMBODIMENTS

Figure 1:
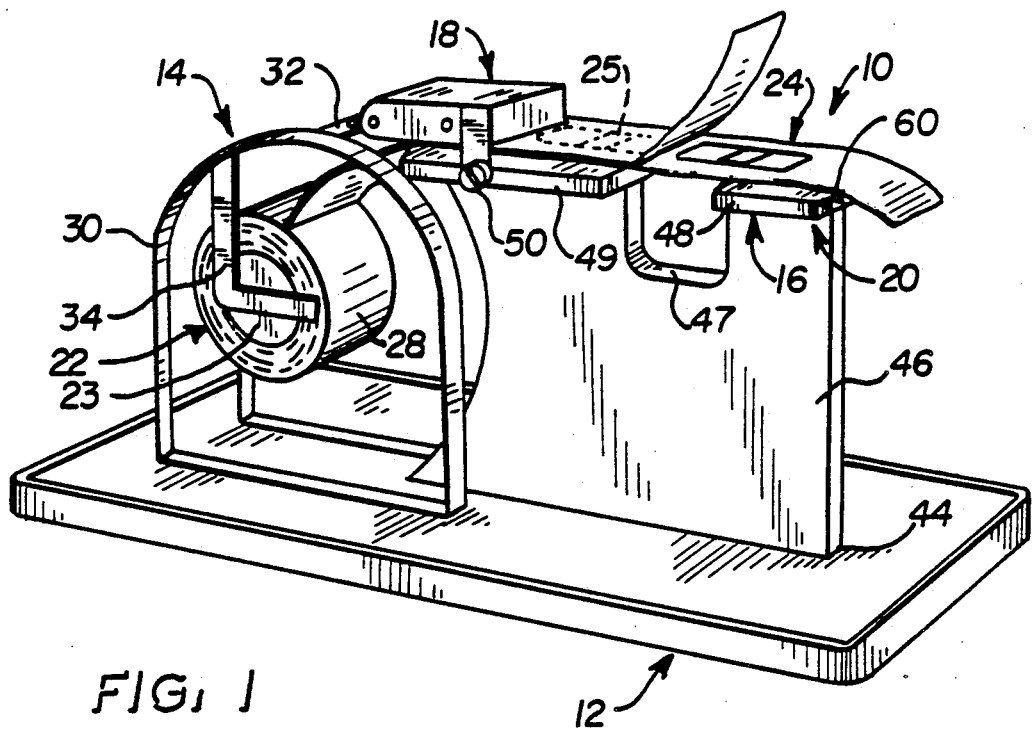
FIG. 1 is a perspective view of the adhesive bandage dispensing device with the adhesive bandage spool mounted thereon.
Figure 2:
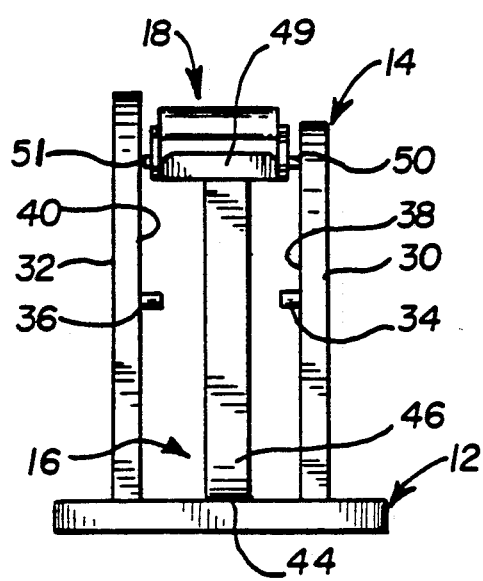
FIG. 2 is a rear elevational view of the device without the bandage spool showing the holder means.
Figure 3:
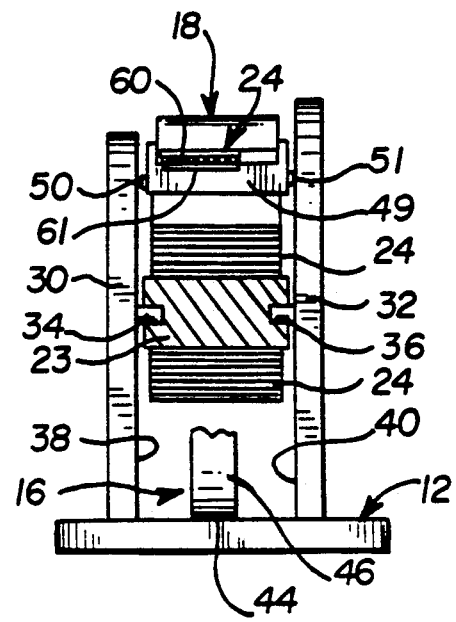
FIG. 3 is a front elevational view, partially in section, of the device showing the spool as mounted.

Referring now more particularly to FIGS. 1-3, the adhesive bandage dispensing device is generally illustrated at 10. The device is comprised of a substantially flat, rectangular base 12, an adhesive bandage carrier spool holder 14 and an adhesive bandage removal platform 16. The adhesive bandage removal platform 16 has a slicer means 18 mounted on one end thereof and a cutter means 20 mounted on the opposite end thereof. The device also includes a removable and separate adhesive bandage carrier spool means 22 with associated cylindrical spool 23 having wound thereon a continuous adhesive bandage strip 24.

The adhesive bandage carrier spool means 22 consists of a cylindrical spool 23 preferably made of plastic with a continuous strip 24 containing a plurality of adhesive bandages 25. This strip 24 will be described in more detail with respect to the discussion of FIGS. 5-7.

The adhesive bandage carrier spool holder 14 holds the carrier spool means 22 in place in the device 10. The spool holder 14 preferably consists of two substantially identical, spaced apart flanges 30 and 32 which are mounted on the base 12 by adhesives or the like or which can be integrally formed with the base 12. The flanges 30, 32 are preferably approximately semicircular in shape but it will be appreciated that any desired shape can be used. Preferably, each flange 30 and 32 has holder means 34 and 36 respectively, which can best be seen in FIG. 2, that are projections from the inner surfaces 38 and 40 of flanges 30 and 32 respectively. These holder means hold the spool 23 in place between the flanges 30 and 32.

It will be appreciated that the flanges 30 and 32 can be made adjustable to move from side to side so as to place more distance between them or from front to back so as to move them further or closer to the front end of the device 10.

The adhesive bandage removal platform 16 is positioned in the center of the base 12 (See FIG. 2) and is also centered (at 44) between the flanges 30 and 32 and can be attached by adhesives or can be integrally formed with the base 12. The platform 16 consists of a longitudinal support 46 with an indentation 47 at its top end and two separate shelves 48 and 49 mounted on top of the support 46. Slicer means 18 is mounted to shelf 49, as by screws 50 and 51. Cutting means 20 is mounted on shelf 48, as by adhesives or the like.

The cutting means 20 is a serrated blade 60 made of steel or aluminum. The blade 60 may be attached to the shelf 48 by adhesives or the like or may be integrally formed with the shelf 48 and is preferably received within a slot (not shown) in the shelf 48. If desired, an attached spring action holder (not shown) built into the shelf 48 can be provided to resist the strip sliding backwards into the housing.

It will be appreciated that the base 12, flanges 30 and 32, longitudinal support 46, and shelves 48 and 49 can be made of materials selected from the group consisting of resinous plastics, aluminum and steel, with resinous plastic being preferred. The blade 60 and parts of the slicer means 18 are preferably made of stainless steel. Also, it will be appreciated that the device can be adopted for vertical wall mounting or other types of mounting besides the bench model illustrated herein.

Figure 4:
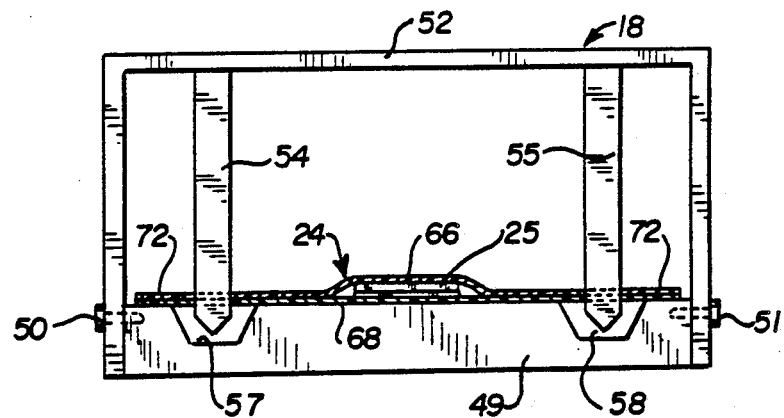
FIG. 4 is a detailed front elevational view of the slicer means, showing a cross sectional view of the continuous strip.

Referring now to FIG. 4, the slicer means 18 consists of a slicer housing 52 which is preferably mounted on shelf 49 by means of screws 50 and 51. Two blades 54 and 55 are in a spaced apart relationship and mounted on the housing 52 so that they are perpendicular to the plane formed by the continuous strip 24. These blades 54 and 55 will slice the upper and lower protective coating 66 and 68. The slicing action, therefore will slice both the upper and lower protective covering 66 and 68. This will be further explained hereinbelow.

Channels 57 and 58 are provided in shelf 49 so that the blades 54 and 55 are long enough to slice through both the top portion 66 and bottom portion 68 of the strip 24.

Figure 5:
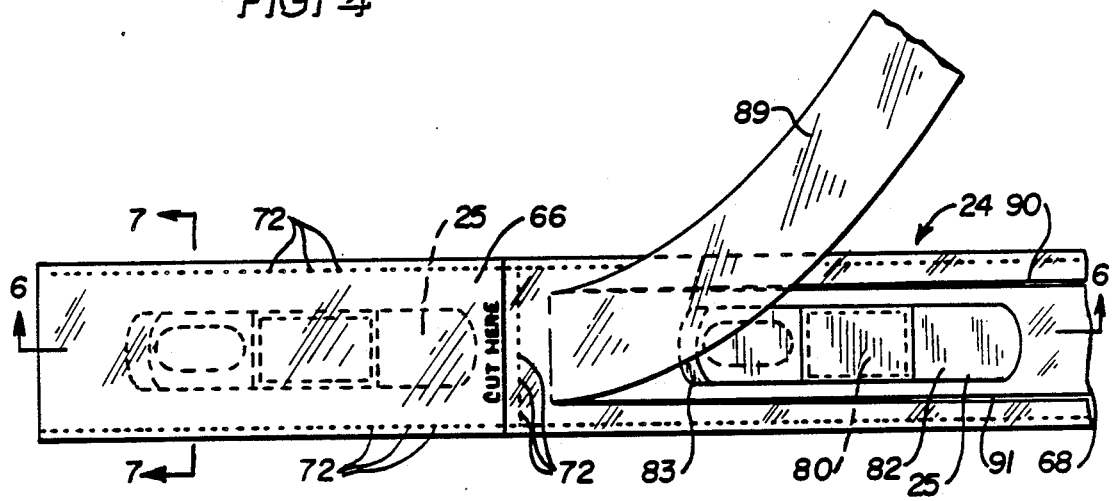
FIG. 5 is a top plan view of a portion of the continuous bandage strip showing two individual bandages thereon, one bandage being covered by the top protective covering and the other bandage being exposed as will occur after slicing of the strip.
Figure 6:
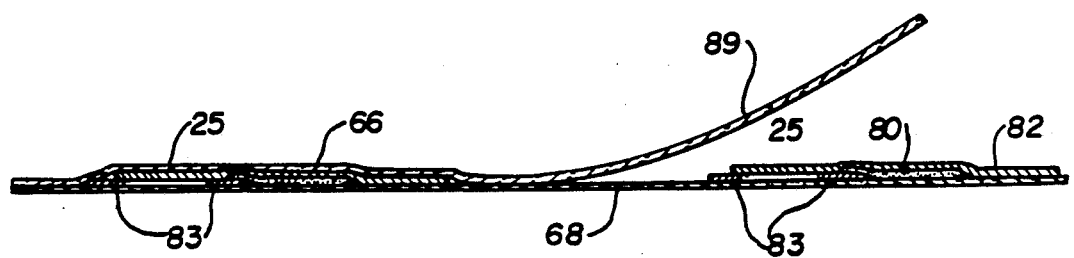
FIG. 6 is a cross-sectional view along line 6—6 of FIG. 2.
Figure 7:
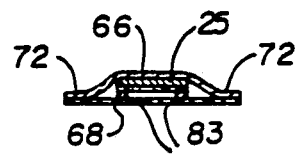
FIG. 7 is a cross-sectional view along line 7—7 of FIG. 2.

Referring now to FIGS. 5–7, the adhesive bandage strip 24 consists of an upper protective strip 66 and a lower protective strip 68, with an individual bandage 25 interposed therebetween. The upper strip 66 is sealed to the lower strip 68 at the points marked by the dots 72 on FIG. 5. The sealing can be done by adhesives or by heat sealing. If desired, a legend such as "CUT HERE", which will indicate to users where to cut the used strip away from the strip 24, can be provided. As can be seen in FIGS. 6 and 7, the upper and lower strips 66 and 68 form a compartment for the individual bandage 25.

The adhesive bandage 25 may be of conventional design having a soft absorbent bandage pad 80 attached to an adhesive coated bandage strip 82. Of course, the adhesive side is facing downward and is mounted on the lower protective strip 68. Preferably, one end of the adhesive strip 82 is attached to a mounting pad 83 which will facilitate removal of the bandage from the lower protective coating 68. The bandage pad 80 is preferably centered on the adhesive strip.

The bandages 25 can be of standard size of approximately 1 ½ to 3 inches in length and ⅜ to ¾ inches in width, but could also be of different sizes and shapes, if desired. Also, different sized bandages could be applied on one continuous strip, but it will be preferred to have one strip contain the same size bandage.

As can be seen in FIGS. 1 and 5, a portion 89 of the upper and lower protective strip is sliced as at 90 and 91 to reveal the adhesive bandage 25. This will be explained further hereinafter with reference to the operation of the device 10.

In use, the spool 23 containing the continuous strip of adhesive bandages 24 is mounted on the holder means 34 and 36 of the respective flanges 30 and 32. The strip 24 is then threaded through the slicer means 18. The strip 24 is pulled away from the spool means 22, the spool 23 being able to rotate about the projections 34 and 36 to feed the strip 24 into the slicer means 18. At this point, the blades 54 and 55 slice the strip 24 so that the top portion 89 can be lifted off the strip 24 so as to gain access to the adhesive bandage 25, as can be seen in FIGS. 1 and 5. The mounting pad 83 is then grasped and the bandage is pulled off of the lower protective coating 68. This allows for one hand operation for removing the bandage 25 from the strip 24. Once the bandage 25 is removed, the bandageless strip is then pulled across shelf 49, indentation 47 and shelf 48 to the edge of shelf 48 where the blade 60 is mounted. At this point, the user pulls the bandageless strip in a downward motion onto blade 60, thus cutting it. The indentation 47 permits the user to insert one finger under the bandageless strip and one over the bandageless strip in order to advance the entire strip so that the blade 60 can sever the bandageless strip portion from the parent strip for subsequent disposal.

It is contemplated that the device will be able to be used with refillable spools of adhesive bandages, although the whole device may be made to be disposable, if desired.

Figure 8:
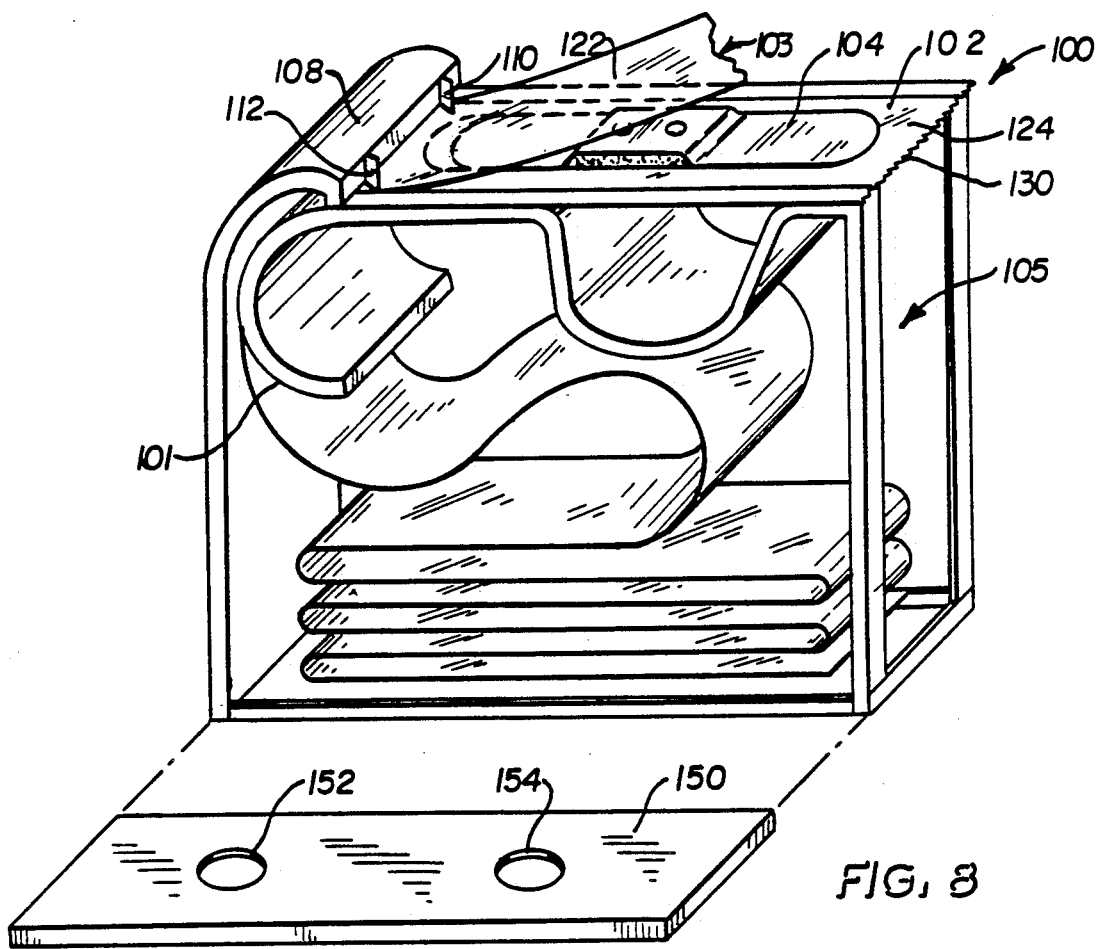
FIG. 8 shows another embodiment of the invention, partially in section, whereby the continuous strip is stored in bulk, as opposed to being wound on a spool.

FIG. 8 shows another embodiment of the device 100. Here, a similar continuous strip 101 having a lower protective coating 102 and an upper protective coating 103 surrounding bandages 104, as was discussed hereinabove, is stacked in a container 105 made of plastic or similar materials. The strip 101 is fed through a curved opening into a slicer means 108, having two blades 110 and 112, which is similar to the slicer means 18 discussed hereinabove. When the strip 102 is pulled through the slicer means 108, the lower and upper protective coating 102 and 103 are sliced, thus enabling a user to lift the top portion 103 from the strip 101 thus exposing bandage 104. The bandage 104 is then ready to be removed from the lower protective coating 102.

After the bandage 104 has been removed, the strip is then pulled over the blade 130 provided on the container 105 in order to remove the bandageless strip from the parent strip 101.

This device can be mounted on a base 150 having upwardly open recesses 152 and 154 in which downwardly projecting bosses (not shown) of the container 105 may be snapped so that the dispenser may be disposed of and the base 150 reused. The base and container may also be permanently mounted, and strips refilled in the container 105, if desired.

Figure 9:
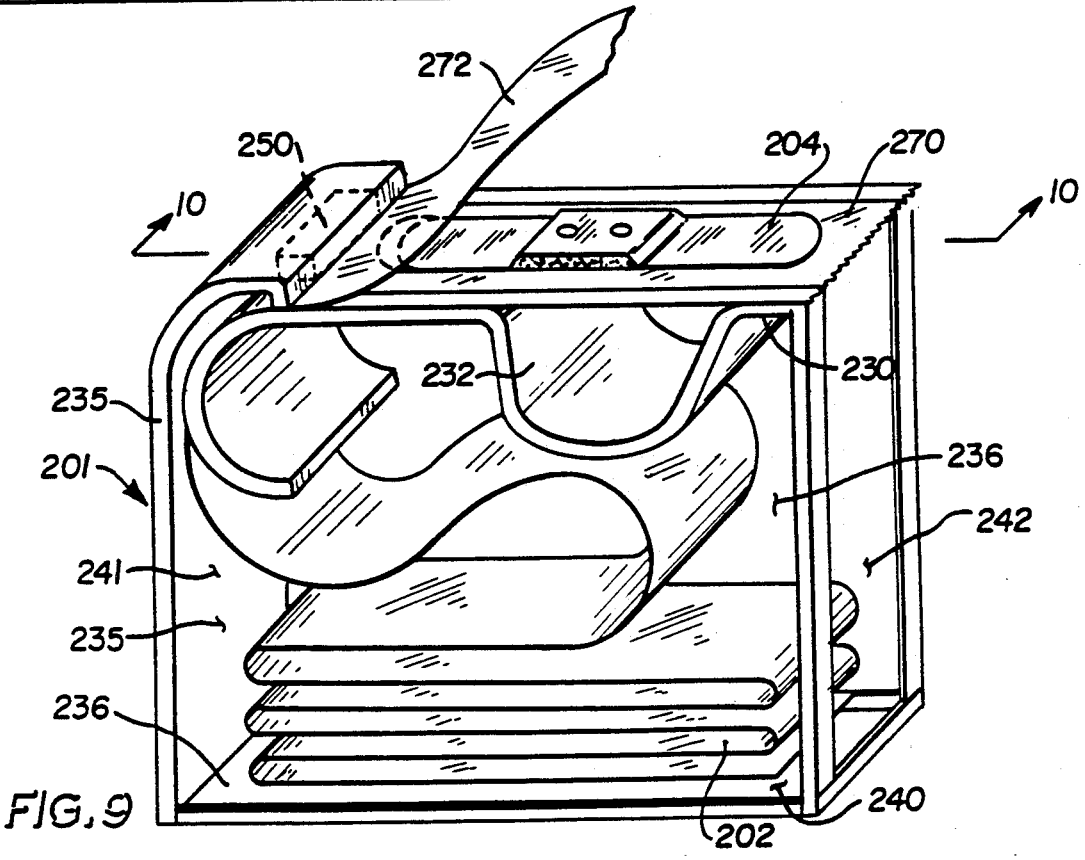
FIG. 9 is a perspective view of yet another embodiment of the invention.
Figure 10:
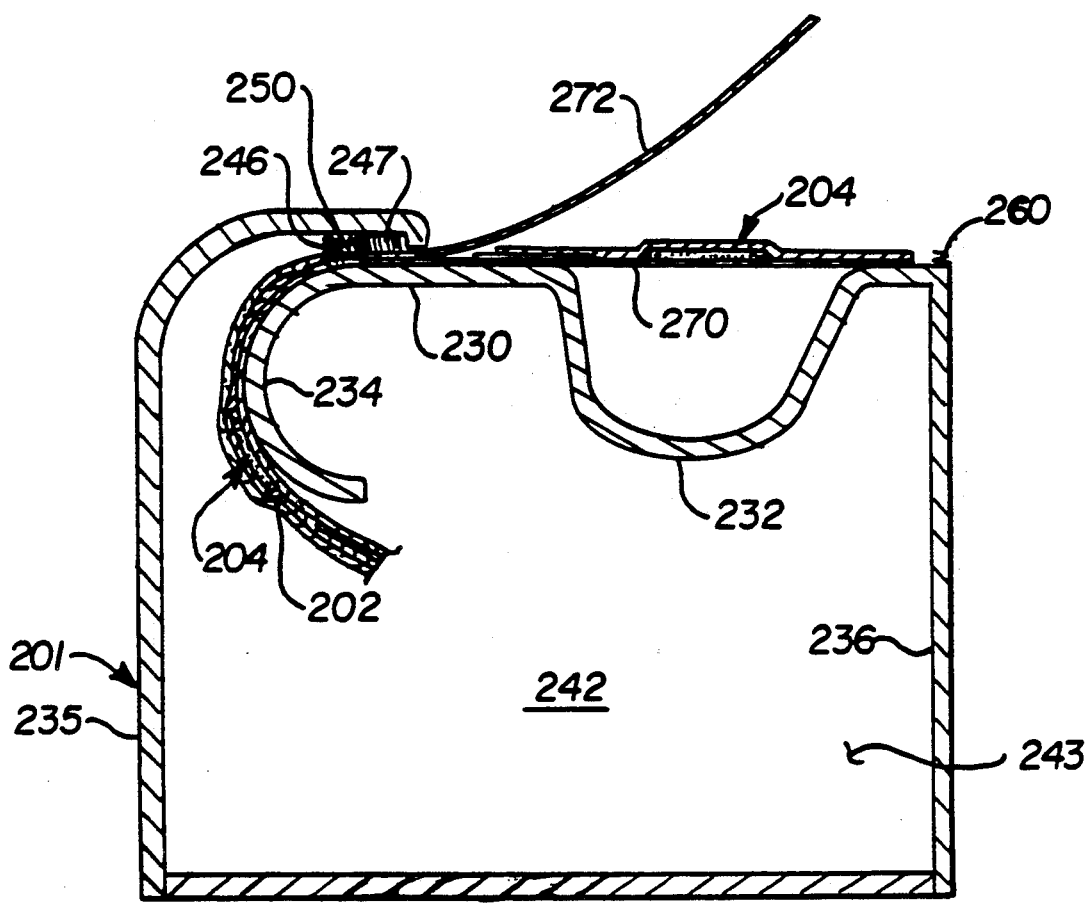
FIG. 10 is a sectional view along line 10—10 of FIG. 9.

Another embodiment of the dispenser of the invention is shown in FIGS. 9 and 10. This dispenser consists of a container 201 made of plastic, in which is disposed a continuous strip 202 containing individual bandages, such as 204.

The dispenser 200 consists of an upper shelf 230 having an indentation 232 and a curved portion 234. The dispenser further consists of sidewalls 235 and 236, a base wall 240, and vertical side panels 241 and 242. These walls form the compartment 243 in which the strip of bandages 202 is disposed. The first sidewall 235, as can be seen in FIG. 10, is designed to curve over and around the curved portion 234 of the upper shelf 230. There is an opening 246 between the curved sidewall 234 and the first sidewall 235 through which the bandage strip 202 can be dispensed.

Associated with sidewall 235 is a sterile barrier 250. This barrier 250 is preferably made of a foam elastomer, rubber or velour. The barrier 250 is spaced from the upper shelf 230 such that a clearance 247 is created that is just about as wide as the height of the bandage strip 202, as can be seen by FIG. 10. This sterile barrier 250 also acts to seal the compartment 243 to resist the entry of dust and dirt. If desired, the sterile barrier 250 can be treated with an antibacterial agent to further sterilize the bandage strip 202.

Figure 11:
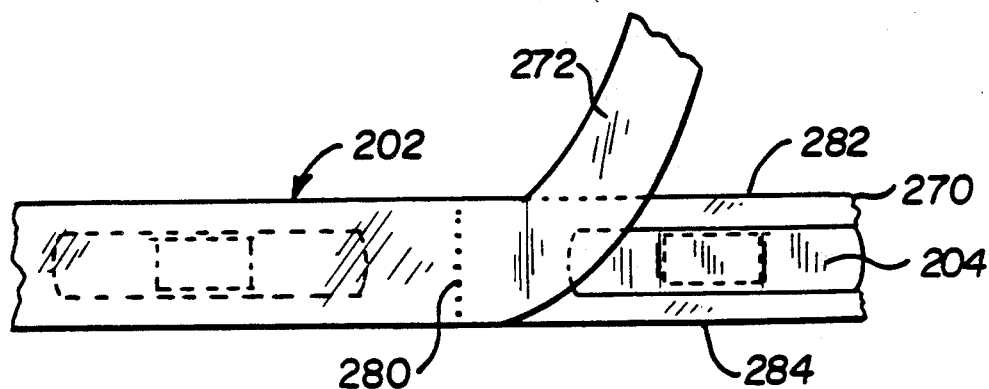
FIG. 11 is a top plan view of the continuous strip used in the embodiment shown in FIG. 10.

The upper shelf 230 has a serrated cutter 260 disposed on the opposite side of the sterile barrier. This cutter can be similar to blade 130 of the embodiment illustrated in FIG. 9. The strip 202, which is shown in greater detail in FIG. 11, consists of a lower protective cover 270 and an upper protective cover 272 with individual bandages 204 disposed therebetween. The lower protective cover 270 is sealed to the upper protective cover 272 only at points 280 indicated by dots. There is no sealing of the strip 202 at its edges 282 and 284 such as with strip 24 described hereinbelow.

In use, the strip 202 is merely removed from the dispenser 200 by pulling the strip over the curved sidewall 234 and through the sterile barrier 250. As the strip 202 is not sealed on its edges 282 and 284, the upper protective cover 272 can be lifted off the strip 202, thus exposing the individual bandage 204. The individual bandage 204 can be mounted to the strip by a method similar to that described with respect to FIGS. 5–7.

After removing the bandage 204 from the strip 202, the bandageless strip can be grasped with help of the indentation 232 and pulled over the cutter 260 for removal from the strip 202.

It will be appreciated that an improved adhesive bandage dispensing device is provided that slices a protective covering of a bandage to allow for quick and efficient one hand access to an adhesive bandage.

Whereas a particular embodiment of the device has been described hereinabove, it will be evident to those skilled in the art that numerous variations of the details may be made without departing from the invention as defined in the appended claims.

We claim:

1. An adhesive bandage dispensing device comprising:
   means for holding a strip of adhesive bandages, said strip having a first layer of material secured to a second layer of material with at least one adhesive bandage disposed therebetween; and
   means for slicing said first and second layer of material along the length of said strip, said slicing means being connected to said holding means, whereby said strip may be removed from said holding means and pulled through said slicing means so as to enable one hand access to said adhesive bandage.

2. The device of claim 1, wherein
   said slicing means has a pair of blades mounted on said holding means, said pair of blades being positioned to slice said first and second layer of material along the length of said strip, on opposite sides of the at least one adhesive bandage disposed in said strip.

3. An adhesive bandage dispensing device comprising:
   means for holding a strip of adhesive bandages, said strip having a first layer of material secured to a second layer of material with at least one adhesive bandage disposed therebetween;
   means for slicing said first and second layer of material, said slicing means being connected to said holding means; and
   means for cutting a portion of said strip from said strip, said cutting means being connected to said holding means, whereby said strip may be removed from said holding means and pulled through said slicer means so as to enable one hand access to said adhesive bandage and whereby said cutter means can be used to separate a portion of said strip from said strip.

4. An adhesive bandage dispensing device comprising
   means for holding a strip of adhesive bandages, said strip having a first layer of material sealingly secured to a second layer of material with at least one adhesive bandage disposed therebetween,
   means for slicing said first and second layer of material, said slicing means being connected to one end of said holding means, and
   means for cutting a portion of said strip from said strip, said cutting means being connected to an opposite end of said holding means, whereby said strip may be removed from said holding means and pulled through said slicer means so as to enable one hand access to said bandage and whereby said cutter means can be used to separate a portion of said strip from said strip.

5. The device of claim 4, wherein
   said slicer means including a housing and two spaced apart blades mounted on said housing.

6. The device of claim 4, including
   a mounting pad interposed between said adhesive and said second layer of material.

7. The device of claim 4, including
   said strip being mounted on a spool.

8. The device of claim 7, wherein
   said holding means includes a base, a spool holder mounted on said base and a longitudinal support having one end connected to a platform and the other end connected to said base.

9. The device of claim 8, wherein
   said spool holder having two spaced apart flanges with associated mounting means, whereby said spool can be rotatably mounted on said spool holder.

10. The device of claim 9, wherein
said longitudinal support mounted generally in the center of said base and centered between said two flanges.

11. The device of claim 10, wherein said platform includes
a first platform spaced apart from a second platform and
said longitudinal support having an indentation between said first platform and said second platform.

12. The device of claim 11, wherein
said slicer means is mounted on said first platform and
said cutting means is mounted on said second platform.

13. The device of claim 12, wherein
said cutting means is a serrated blade.

14. The device of claim 7, wherein
said holding means includes a base and a container mounted on said base.

15. The device of claim 14, wherein
said strip is housed in said container.

16. The device of claim 15, wherein
said container is removably mounted on said base.

17. A method for dispensing bandages comprising the steps of:
providing means for holding a strip of adhesive bandages, said strip having a first layer of material secured to a second layer of material with at least one adhesive bandage disposed therebetween;
providing means for slicing said first and second layer of material along the length of said strip, said slicing means being connected to said holding means;
removing said strip from said holding means; and
said slicing means slicing said first and second layer of material along the length of said strip, whereby said adhesive bandage may be removed from between said first and second layer of material.

18. The method of claim 17, further comprising the step of cutting a portion of said strip from said strip.

* * * * *

UNITED STATES PATENT AND TRADEMARK OFFICE
CERTIFICATE OF CORRECTION

PATENT NO. : 4,993,586

DATED : February 19, 1991

INVENTOR(S) : ORRIN E. TAULBEE, deceased, et al.

It is certified that error appears in the above-identified patent and that said Letters Patent is hereby corrected as shown below:

On the Title Page, the Inventors should read as follows:

--Orrin E. Taulbee, deceased, late of Pittsburgh, PA, by Laura J. Harper, executrix, Blacksburg, VA and Gregor M. Taulbee, executor, Columbus, OH; and Frank R. Walters, Pittsburgh, PA--.

Signed and Sealed this

Twentieth Day of October, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO. : 4,993,586

DATED : February 19, 1991

INVENTOR(S) : ORRIN E. TAULBEE ET AL.

It is certified that error appears in the above-identified patent and that said Letters Patent is hereby corrected as shown below:

Column 1, line 53, after "slicer", the following should be inserted: --means. This will expose a separate adhesive bandage which--.

Signed and Sealed this

Fifteenth Day of December, 1992

Attest:

DOUGLAS B. COMER

Attesting Officer     Acting Commissioner of Patents and Trademarks